United States Patent
Toida

(10) Patent No.: US 7,880,892 B2
(45) Date of Patent: Feb. 1, 2011

(54) OPTICAL TOMOGRAPHIC IMAGING APPARATUS AND OPTICAL TOMOGRAPHIC IMAGING METHOD

(75) Inventor: Masahiro Toida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 12/493,544

(22) Filed: Jun. 29, 2009

(65) Prior Publication Data
US 2009/0323080 A1 Dec. 31, 2009

(30) Foreign Application Priority Data
Jun. 30, 2008 (JP) ............................. 2008-170501

(51) Int. Cl.
G01B 9/02 (2006.01)
G01B 11/02 (2006.01)
(52) U.S. Cl. ...................... 356/479; 356/497
(58) Field of Classification Search ................ 356/479, 356/497
See application file for complete search history.

(56) References Cited

U.S. PATENT DOCUMENTS

| 6,680,779 | B2   | 1/2004  | Toida                      |
|-----------|------|---------|----------------------------|
| 6,687,010 | B1 * | 2/2004  | Horii et al. ........... 356/479 |
| 7,133,138 | B2 * | 11/2006 | Horii et al. ........... 356/497 |
| 7,508,524 | B2 * | 3/2009  | Mahadevan-Jansen et al. ... 356/479 |
| 7,538,884 | B2 * | 5/2009  | Teramura et al. ........ 356/489 |
| 7,570,364 | B2 * | 8/2009  | Kuroiwa ............... 356/479 |
| 2007/0239035 | A1 * | 10/2007 | Nakabayashi ........... 600/476 |
| 2008/0117427 | A1 * | 5/2008  | Teramura et al. ........ 356/484 |
| 2008/0117431 | A1 * | 5/2008  | Teramura .............. 356/511 |
| 2009/0021724 | A1 * | 1/2009  | Mahadevan-Jansen et al. ... 356/73 |
| 2010/0210952 | A1 * | 8/2010  | Taira et al. ........... 600/476 |

FOREIGN PATENT DOCUMENTS
JP 2002-14037 A 1/2002

OTHER PUBLICATIONS
Zhang et. al. "Coherent amplified optical coherence tomography", Proc. of SPIE-OSA Biomedical Optics, SPIE vol. 6627, 662718 (2007).

* cited by examiner

*Primary Examiner*—Patrick J Connolly
(74) *Attorney, Agent, or Firm*—Birch, Stewart, Kolasch & Birch, LLP

(57) ABSTRACT

In an optical tomographic imaging apparatus, a wavelength of a light beam emitted from the light source is selected by a light source section filter, and the light beam emitted from the light source is split into a measurement light beam and a reference light beam. The measurement light beam is reflected from a measurement subject when the measurement light beam is irradiated, is amplified. A specific wavelength from the amplified reflected light beam is selected by an amplifying section filtering mechanism having a filter characteristic identical to a time variation characteristic of the light source section filter, and then the reflected light beam is multiplexed with the reference light beam. A tomographic image of the measurement subject is acquired from detection result of an interference light beam between the reflected light beam and the reference light beam which have been multiplexed.

12 Claims, 11 Drawing Sheets

OPTICAL TOMOGRAPHIC IMAGING APPARATUS AND OPTICAL TOMOGRAPHIC IMAGING METHOD

BACKGROUND OF THE INVENTION

1. Field of the Invention

The present invention relates to an optical tomographic imaging apparatus, and in particular, to an S/N enhancement technique in optical coherence tomography (OCT) measurement which is not restricted by the light intensity of a light beam irradiated on a subject to be examined.

2. Description of the Related Art

Conventionally, there are known optical tomographic imaging apparatuses utilizing optical coherence tomography (OCT) measurement as a method of acquiring a tomographic image without dissecting a measurement subject such as living tissue.

OCT measurement is an optical interferometric measurement method in which a light beam emitted from a light source is divided into two light beams, namely, a measurement light beam and a reference light beam, and which utilizes the fact that optical interference is only detected when respective optical path lengths of the measurement light beam and the reference light beam match each other within the range of a coherence length of the light source.

For example, an optical tomographic imaging apparatus is known that is an application to SS-OCT (swept source OCT) of the concept of an S/N enhancement technique using light amplification in TD-OCT (time-domain OCT), wherein by optically amplifying a reflected light beam reflected off of a measured section and then causing the reflected light beam to interfere with a reference light beam, and by measuring the intensity of the interference light beam, S/N can be enhanced while maintaining signal light intensity is maintained at a level where the safety of the measured section can be secured (for example refer to Jun Zhang et. al. "Coherent amplified optical coherence tomography", Proc. of SPIE-OSA Biomedical Optics, SPIE Vol. 6627, 662718 (2007)).

SUMMARY OF THE INVENTION

However, with the optical tomographic imaging apparatus according to aforementioned "Coherent amplified optical coherent tomography," there is a problem in that sufficient S/N enhancement cannot be achieved due to the co-presence of fluctuations of a spontaneous emission light beam from a light amplifying medium and noise due to intrinsic light fluctuations from the light source in an AC component of the interference light beam.

The present invention has been made in consideration of such circumstances, and an object thereof is to provide an optical tomographic imaging apparatus and method capable of reducing noise due to a spontaneous emission light beam generated from a light amplifying medium and effectively enhancing S/N.

In order to achieve the object described above, a first aspect of the present invention provides an optical tomographic imaging apparatus including: a light source unit including a light source that emits a light beam having a certain wavelength band, and a wavelength selecting device as a light source section filter that selects a wavelength of the light beam emitted from the light source; a light splitting device that splits the light beam emitted from the light source unit into a measurement light beam and a reference light beam; an optical path length adjusting device that adjusts an optical path length of the reference light beam split by the light splitting device; a light amplifying device that amplifies a reflected light beam from a measurement subject when the measurement light beam split by the light splitting device is irradiated on the measurement subject; an amplifying section filtering mechanism having a filter characteristic identical to a time variation characteristic of the light source section filter, and which selects a specific wavelength from the amplified reflected light beam; an optical multiplexing device that multiplexes the reflected light beam from which the specific wavelength has been selected by the amplifying section filtering mechanism with the reference light beam whose optical path length has been adjusted by the optical path length adjusting device; an interference light detecting device that detects an interference light beam between the reflected light beam and the reference light beam multiplexed by the optical multiplexing device; and an image acquiring device that acquires a tomographic image of the measurement subject from the interference light beam detected by the interference light detecting device.

Accordingly, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized. Furthermore, since unnecessary light beams can be prevented from being introduced to a detector, saturation of a photodetector can be prevented.

In addition, according to a second aspect of the present invention, the wavelength selecting device as the light source section filter and the amplifying section filtering mechanism can be separately configured.

Furthermore, according to a third aspect of the present invention, the wavelength selecting device as the light source section filter and the amplifying section filtering mechanism can share at least a part of each other.

In addition, according to a fourth aspect of the present invention, the wavelength selecting device as the light source section filter and the amplifying section filtering mechanism can use polygon mirrors.

Furthermore, according to a fifth aspect of the present invention, the wavelength selecting device as the light source section filter and the amplifying section filtering mechanism can share a polygon mirror, and respectively use different faces of the polygon mirror.

In addition, according to a sixth aspect of the present invention, the wavelength selecting device as the light source section filter and the amplifying section filtering mechanism can share a polygon mirror and use one face of the polygon mirror differentiatingly (separately) using an upper part and a lower part of the one face.

Furthermore, according to a seventh aspect of the present invention, the wavelength selecting device as the light source section filter and the amplifying section filtering mechanism can use galvano scanners.

In addition, according to an eighth aspect of the present invention, the wavelength selecting device as the light source section filter and the amplifying section filtering mechanism can use Fabry-Perot filters.

As shown, by sharing at least a part of a filter structure using various configurations, an apparatus structure can be downsized to a certain degree.

Furthermore, according to a ninth aspect of the present invention, a transmission band of the amplifying section filtering mechanism can be wider than a transmission band of the wavelength selecting device as the light source section filter.

Accordingly, synchronization between the light source section filter and the amplifying section filtering mechanism can be achieved with greater ease.

In addition, according to a tenth aspect of the present invention, the light amplifying device can be a semiconductor gain medium.

Accordingly, by using a semiconductor gain medium, a compact configuration can be realized with less cost.

Furthermore, according to an eleventh aspect of the present invention, the light amplifying device can be an optical fiber amplifier.

Accordingly, since amplification can be increased by extending an optical fiber, a high gain can be realized.

Further, a method which includes steps and functions performed by the optical tomographic imaging apparatus according to any of the aspects of the present invention can also achieve the object of the present invention.

As described above, according to the present invention, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized. Furthermore, since unnecessary light beams can be prevented from being introduced to a detector, saturation of a photodetector can be prevented.

BRIEF DESCRIPTION OF THE DRAWINGS

FIG. 10A is a configuration diagram showing a wavelength selecting device according to the sixth embodiment while

DETAILED DESCRIPTION OF THE PREFERRED EMBODIMENTS

An optical tomographic imaging apparatus according to the present invention will now be described in detail with reference to the attached drawings.

Figure 1:
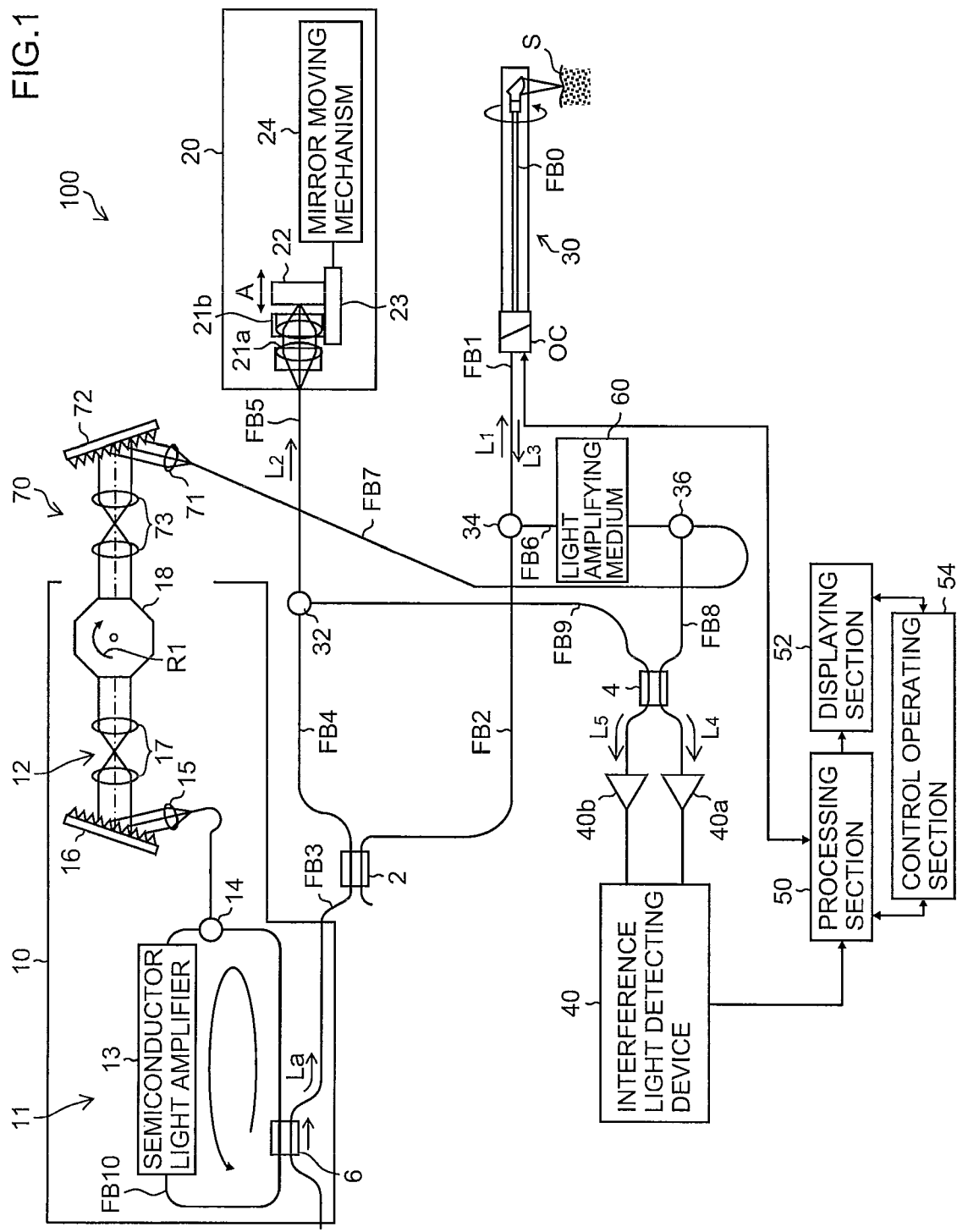
FIG. 1 is a schematic configuration diagram showing a first embodiment of an optical tomographic imaging apparatus according to the present invention.

FIG. 1 is a schematic configuration diagram showing a first embodiment of an optical tomographic imaging apparatus according to the present invention.

As shown in FIG. 1, an optical tomographic imaging apparatus 100 according to the present embodiment acquires a tomographic image of a measurement subject such as living tissue or a cell inside, for example, a body cavity through SS-OCT (swept source OCT) measurement. The optical tomographic imaging apparatus 100 includes: a light source unit 10 that emits light beams; an optical path length adjusting device 20 that adjusts an optical path length of a reference light beam L2 split by a light splitting device 2 which splits a light beam La emitted from the light source unit 10 into a measurement light beam L1 and the reference light beam L2; a probe 30 that guides the measurement light beam L1 split by the light splitting device 2 to a measurement subject S; an optical multiplexing device 4 that multiplexes a reflected light beam L3 reflected off of the measurement subject S (subject to be measured) when the measurement light beam L1 from the probe 30 is irradiated thereon with the reference light beam L2; an interference light detecting device 40 that detects an interference light beam L4 of the reflected light beam L3 and the reference light beam L2 multiplexed by the optical multiplexing device 4; a processing section (image acquiring device) 50 that detects an intensity of the interference light beam L4 at each depth position of the measurement subject 3 and acquires a tomographic image of the measurement subject S by analyzing the frequency of an interference signal detected by the interference light detecting device 40; a control operating section 54 that controls a displaying section 52 which displays the acquired tomographic image as well as the respective sections, and the like.

Moreover, the present embodiment is arranged so as to effectively enhance S/N by amplifying the reflected light beam L3 from the measurement subject S, filtering out an unnecessary spontaneous emission light beam generated by the light amplifying section other than an induced emission light beam, and causing the reflected light beam L3 to interfere with the reference light beam L2.

To this end, the optical tomographic imaging apparatus 100 according to the present embodiment further includes: a light amplifying medium 60 for amplifying the reflected light beam L3; and an amplifying section filtering mechanism 70 that filters out unnecessary spontaneous emission light beams. A detailed description thereof will be included in the following description of the configurations of the respective sections.

The light source unit 10 emits a laser beam La while sweeping frequencies at regular periods. To this end, the light source unit 10 includes: a light source 11 that emits a light beam having a certain wavelength band; and a wavelength selecting device 12 as a wavelength sweeping light source filter (light source section filter) that selects a wavelength emitted from the light source 11. The light source 11 comprises a semiconductor light amplifier (semiconductor gain medium) 13, connected in a loop configuration to an optical fiber FB10, which emits a spontaneous emission light beam and amplifies a spontaneous emission light beam guided through the optical fiber FB10. The light source 11 functions to emit the spontaneous emission light beam to the side of one end of the optical fiber FB10 in response to the injection of a drive current, and to amplify a light beam that enters from the side of the other end of the optical fiber FB10. In addition, when the drive current is supplied to the semiconductor light amplifier 13, the laser beam La is to be emitted to an optical fiber FB11 from a laser light source resonator formed by the semiconductor light amplifier 13 and the optical fiber FB10.

The wavelength selecting device 12 is arranged so as to select a wavelength of a spontaneous emission light beam that guides the optical fiber FB10 as a wavelength sweeping light source filter (light source section filter), and is arranged so that the spontaneous emission light beam enters via the optical fiber FB11 from an optical branching unit (circulator) 14 coupled to the optical fiber FB10. The wavelength selecting device 12 includes: a collimator lens 15; a diffraction grating element 16; an optical system (optical face tangle error correcting lens) 17; a rotary polygon mirror (polygon mirror) 18, and the like.

A light beam entering from the optical fiber FB11 is reflected by the rotary polygon mirror 18 via the collimator lens 15, the diffraction grating element 16, and the optical system 17. The reflected light beam reenters the optical fiber FB11 via the optical system 17, the diffraction grating element 16, and the collimator lens 15.

The rotary polygon mirror (polygon mirror) 18 is arranged so as to rotate in the direction of arrow R1 such that the angle of each reflecting face changes with respect to an optical axis of the optical system 17. Accordingly, only a light beam of a specific frequency range among light beams separated at the diffraction grating element 16 returns to the optical fiber FB11.

The frequency of the light beam that returns to the optical fiber FB11 is determined by an angle formed by the optical axis of the optical system 17 and a reflecting face of the rotary polygon mirror 18. A light beam of a specific frequency range entering the optical fiber FB11 enters the optical fiber FB10 from the optical branching unit 14 and, as a result, the laser beam La of a specific frequency range is emitted to the side of an optical fiber FB3 from an optical fiber coupler 6.

Therefore, since the angle formed by the optical axis of the optical system 17 and the reflecting face of the rotary polygon mirror 18 changes at a certain rate when the rotary polygon mirror 18 rotates at a constant speed in the direction of arrow R1, the wavelength of the light beam reentering the optical fiber FB11 is to be swept at regular periods (at a regular cycle). In other words, the laser beam La whose wavelength is swept at regular periods is emitted from the light source unit 10 to the side of the optical fiber FB3 via the optical fiber coupler 6.

The light splitting device 2 includes, for example, 2×2 optical fiber couplers, and is arranged so as to split the laser beam La guided from the light source unit 10 via the optical fiber FB3 into the measurement light beam L1 and the reference light beam L2. The light splitting device 2 is optically connected to two optical fibers FB2 and FB4 respectively, whereby the measurement light beam L1 is to be guided to the side of the optical fiber FB2 while the reference light beam L2 is to be guided to the side of the optical fiber FB4.

One tip of the optical fiber FB4 is connected to an optical branching unit (circulator) 32. An optical fiber FB5 and an optical fiber FB9 are further connected to the optical branching unit 32. The reference light beam L2 guided from the optical fiber FB4 is guided from the optical branching unit 32 to the optical fiber FB5. Moreover, the optical path length adjusting device 20 is disposed ahead of the optical fiber FB5.

The optical path length adjusting device 20 is arranged so as to change the optical path length of the reference light beam L2 in order to adjust the position where the acquisition of a tomographic image is to be commenced. The optical path length adjusting device 20 includes: a reflecting mirror 22 that reflects the reference light beam L2 emitted from the optical fiber FB5; a first optical lens 21a disposed between the reflecting mirror 22 and the optical fiber FB5; and a second optical lens 21b disposed between the first optical lens 21a and the reflecting mirror 22.

The first optical lens 21a functions to convert the reference light beam L2 emitted from the optical fiber FB5 into a parallel light beam, and to collect the reference light beam L2 reflected off of the reflecting mirror 22 onto the core of the optical fiber FB5. In addition, the second optical lens 21b functions to collect the reference light beam L2 converted into a parallel light beam by the first optical lens 21a onto the reflecting mirror 22, and to convert the reference light beam L2 reflected off of the reflecting mirror 22 into a parallel light beam.

Accordingly, the reference light beam L2 emitted from the optical fiber FB5 is converted into a parallel light beam by the first optical lens 21a and collected onto the reflecting mirror 22 by the second optical lens 21b. Subsequently, the reference light beam L2 reflected off of the reflecting mirror 22 is converted into a parallel light beam by the second optical lens 21b and collected onto the core of the optical fiber FB5 by the first optical lens 21a.

Furthermore, the optical path length adjusting device 20 includes: a movable stage 23 that fixes the second optical lens 21b and the reflecting mirror 22; and a mirror moving mechanism 24 that moves the movable stage 23 in the direction of the optical axis of the first optical lens 21a. The optical length of the reference light beam L2 changes in correspondence with the movement of the movable stage 23 in the direction of arrow A.

A light beam whose optical path length has been changed by the optical path length adjusting device 20 reenters the optical fiber FB5, and is further guided to the side of the optical fiber FB9 via the optical branching unit 32.

On the other hand, an optical branching unit (circulator) 34 is connected ahead of the optical fiber FB2 that guides the measurement light beam L1. An optical fiber FB1 and an optical fiber FB6 are further connected to the optical branching unit 34, whereby the measurement light beam L1 is guided to the side of the optical fiber FB1 from the optical branching unit 34.

The probe 30 is optically connected to one tip of the optical fiber FB1, whereby the measurement light beam L1 is to be guided from the optical fiber FB1 to an optical fiber FB0 inside the probe 30. The probe 30 is to be, for example, inserted into a body cavity via a forceps channel from a forceps opening, and is removably mounted to the optical fiber FB1 by an optical connector OC.

The probe 30 is connected to the optical fiber FB1 via the optical connector OC, whereby the measurement light beam L1 guided by the optical fiber FB1 enters the optical fiber FB0 inside the probe 30. The entered measurement light beam L1 is transmitted by the optical fiber FB0 and is irradiated on the measurement subject S. In addition, the returning light beam (reflected light beam) L3 reflected off of the measurement subject S is arranged so as to reenter the optical fiber FB0 and emitted to the optical fiber FB1 via the optical connector OC.

The reflected light beam L3 having entered the optical fiber FB1 is guided to the side of the optical fiber FB6 via the optical branching unit 34.

Moreover, the light amplifying medium 60 is disposed on the optical fiber FB6. The light amplifying medium 60 is not restricted to any particular form and can be favorably exemplified by, for example, a semiconductor gain medium (SOA: semiconductor optical amplifier) or an optical fiber amplifier (OFA).

A semiconductor gain medium (SOA) is an element having a light amplifying medium of a striped optical waveguide and which amplifies a signal light beam without performing electrical conversion thereon. While an SOA basically shares the same structure as a semiconductor laser, the SOA is designed so as not to take an optical resonator structure by suppressing the optical reflectance of element ends using nonreflective coating or the like. Accordingly, the SOA is arranged so that lasing of the SOA itself is suppressed even when a carrier is injected, and an amplified light beam is emitted through induced emission by an input signal light beam.

In addition, an optical fiber amplifier (OFA) is arranged so that when a signal light beam is inputted together with an intense excitation light beam to a light amplifying optical fiber impregnated with erbium, praseodymium or the like, the signal light beam is amplified by acquiring energy from the excitation light beam.

An optical branching unit (circulator) 36 is disposed at the other end of the optical fiber FB6 on which the light amplifying medium 60 is provided. An optical fiber FB7 and an optical fiber FB8 are further connected to the optical branching unit 36. The reflected light beam L3 amplified by the light amplifying medium 60 is guided to the side of the optical fiber FB7 via the optical branching unit 36. Moreover, the amplifying section filtering mechanism 70 is disposed ahead of a tip of the optical fiber FB7. It should be noted that, hereinafter, the amplifying section filtering mechanism may sometimes be simply referred to as the filtering mechanism.

Since the light amplifying medium 60 amplifies a signal light beam (reflected light beam L3) but emits an unnecessary spontaneous emission light beam at the same time, the filtering mechanism 70 is provided so as to filter out the unnecessary spontaneous emission light beam.

As shown in FIG. 1, the filtering mechanism 70 has the same configuration as the wavelength selecting device 12 (wavelength sweeping light source filter), and shares the rotary polygon mirror 18 of the wavelength selecting device 12. That is, the filtering mechanism 70 includes a collimator lens 71, a diffraction grating element 72, and an optical system 73, and is arranged so that a light beam entering the collimator lens 71 from the optical fiber FB7 enters a face opposing (or parallel to) a face of the rotary polygon mirror 18, to which a light beam enters from the optical system 17 of the wavelength selecting device 12 via the diffraction grating element 72 and the optical system 73. A light beam reflected off of the face of the rotary polygon mirror 18 reenters the optical fiber FB7 via the optical system 73, the diffraction grating element 72, and the collimator lens 71.

With the filtering mechanism 70, the light source unit 10 and the rotary polygon mirror 18 are shared. Only light beams having the same wavelength among the amplified reflected light beam L3 are selected in synchronization with a light beam oscillated by the light source unit 10 using another face of the rotary polygon mirror 18, and the selected light beams are arranged so as to return to the side of the optical fiber FB7. Subsequently, the reflected light beam L3 is caused to interfere with the reference light beam L2. As shown, with the filtering mechanism 70, S/N deterioration is prevented by filtering out an unnecessary spontaneous emission light beam generated at the light amplifying medium 60.

The face of the rotary polygon mirror 18 to which a light beam enters from the optical system 73 need not necessarily be a face that is parallel to the face to which a light beam enters from the optical system 17 of the wavelength selecting device 12 as described above, and any of different faces shall suffice, such as a face angled 90 degrees from the face to which a light beam enters from the optical system 17 of the wavelength selecting device 12.

A light beam reentering the optical fiber FB7 from the filtering mechanism 70 is guided from the optical fiber FB7 to the optical fiber FB8 via the optical branching unit 36. Meanwhile, the reference light beam L2 whose optical path length has been changed by the optical path length adjusting device 20 is guided to the side of the optical fiber FB9 via the optical fiber FB5 and the optical branching unit 32.

The reflected light beam L3 guided by the optical fiber FB8 and the reference light beam L2 guided by the optical fiber FB9 are multiplexed by the optical multiplexing device 4 and are outputted as interference light beams L4 and L5. The interference light beam L4 is arranged so as to enter a detector 40a, while the interference light beam L5 is arranged so as to enter a detector 40b.

The interference light detecting device 40 is arranged so as to detect interference light beams L4 and L5 generated by multiplexing the reference light beam L2 and the amplified reflected light beam L3 as interference signals. In addition, the interference light detecting device 40 functions to adjust the balance of intensities between the interference light beams L4 and L5 outputted from the optical multiplexing device 4 based on the detection results of the detectors 40a and 40b.

A processing section 50 detects a region at a measurement position in which the probe 30 and the measurement subject S are in contact with each other or, more precisely, a region at which a surface of a probe outer casing of the probe 30 and a surface of the measurement subject S are in contact with each other from an interference signal detected by the interference light detecting device 40. In addition, the processing section 50 acquires a tomographic image from an interference signal detected by the interference light detecting device 40.

The displaying section 52 is made up of a CRT, a liquid crystal display device, or the like, and displays a tomographic image transmitted from the processing section 50.

The control operating section 54 includes an input device such as a keyboard or a mouse and a control device that manages various conditions based on inputted information, and is connected to the processing section 50 and the displaying section 52. Based on an operator's instruction inputted via the input device, the control operating section 54 performs inputting, setting, and changing of various processing conditions and the like at the processing section 50 as well as changing and the like of display settings of the displaying section 52.

Operations of the optical tomographic imaging apparatus 100 according to the present embodiment will be described below.

First, by moving the movable stage 23 in the direction of arrow A using the mirror moving mechanism 24 of the optical path length adjusting device 20 shown in FIG. 1, an optical path length is adjusted and set so that the measurement subject S is positioned in the measurable region.

Subsequently, the laser beam La is emitted from the light source unit 10. The emitted laser beam La is split into the measurement light beam L1 and the reference light beam L2 by the light splitting device 2. The measurement light beam L1 is guided from the optical fiber FB2 to the optical connector OC via the optical branching unit 34 and the optical fiber FB1. In addition, the measurement light beam L1 is guided from the optical connector OC to the optical fiber FB0 inside the probe 30 and is irradiated on the measurement subject S. At this point, since the optical fiber FB0 inside the probe 30 is being rotated, the measurement light beam L1 irradiates the measurement subject S including a body cavity or the like across the entire periphery thereof.

A light beam reflected at each depth position of the measurement subject S enters the optical fiber FB0 of the probe 30 as the reflected light beam (returning light beam) L3, and is guided from the optical fiber FB0 to the optical fiber FB1 via the optical connector OC. Subsequently, the reflected light beam L3 is guided to the optical fiber FB6 via the optical branching unit 34, and is amplified by the light amplifying medium 60. The amplified reflected light beam L3 is guided to the optical fiber FB7 via the optical branching unit 36.

An unnecessary spontaneous emission light beam is filtered out by the filtering mechanism 70 from the amplified reflected light beam L3 guided to the optical fiber FB7 so that only a light beam of a specific wavelength is extracted therefrom, and the extracted light beam is once again guided to the optical fiber FB7. Subsequently, the reflected light beam L3 is guided to the optical fiber FB8 via the optical branching unit 36, and enters the optical multiplexing device 4.

Meanwhile, the reference light beam L2 split by the light splitting device 2 enters the optical path length adjusting device 20 from the optical fiber FB4 via the optical branching unit 32 and the optical fiber FB5. The reference light beam L2 whose optical path length has been adjusted by the optical path length adjusting device 20 reenters the optical fiber FB5. Subsequently, the reference light beam L2 having entered the optical fiber FB5 is guided to the optical fiber FB9 via the optical branching unit 32, and enters the optical multiplexing device 4 from the optical fiber FB9.

The optical multiplexing device 4 multiplexes the reflected light beam L3 reflected off of the measurement subject S, amplified by the light amplifying medium 60 and from which an unnecessary spontaneous emission light beam is filtered out by the filtering mechanism 70, with the reference light beam L2 whose optical path length has been adjusted by the optical path length adjusting device 20.

Accordingly, the reflected light beam L3 and the reference light beam L2 are multiplexed and the interference light beams L4 and L5 are generated. The interference light beams L4 and L5 are detected as an interference signal by the interference light detecting device 40 via the detectors 40a and 40b.

The detected interference signal is sent to the processing section 50. Upon acquisition of the transmitted interference signal, the processing section 50 acquires information regarding a measurement position from the optical connector OC and associates the interference signal with the positional information of the measurement position. Subsequently, from the information, the processing section 50 generates a depth-direction tomographic image with respect to a contact region of the outer casing of the probe 30 and the measurement subject S. The generated tomographic image is transmitted to the displaying section 52 to be displayed.

As shown, in the present embodiment, the reflected light beam L3 is amplified by the light amplifying medium 60 for the purpose of enhancing S/N. However, since the light amplifying medium 60 emits spontaneous emission light (amplified spontaneous emission (ASE) light) in addition to light emitted through so-called induced emission, the rotary polygon mirror 18 is shared in the same manner as the wavelength selecting device 12 of the light source unit 10 so that a spontaneous emission light beam is filtered out by the filtering mechanism 70 using another face of the rotary polygon mirror 18.

As a result, since a spontaneous emission light beam from a light amplifying medium unnecessary for interference can be blocked, S/N deterioration due to fluctuations in the spontaneous emission light beam can be prevented, and S/N enhancement equivalent to a gain of a light amplifying section can be realized. Furthermore, since an unnecessary light beam can be prevented from being introduced to a detector, saturation of a photodetector can be prevented.

A second embodiment of the present invention will now be described.

Figure 2:
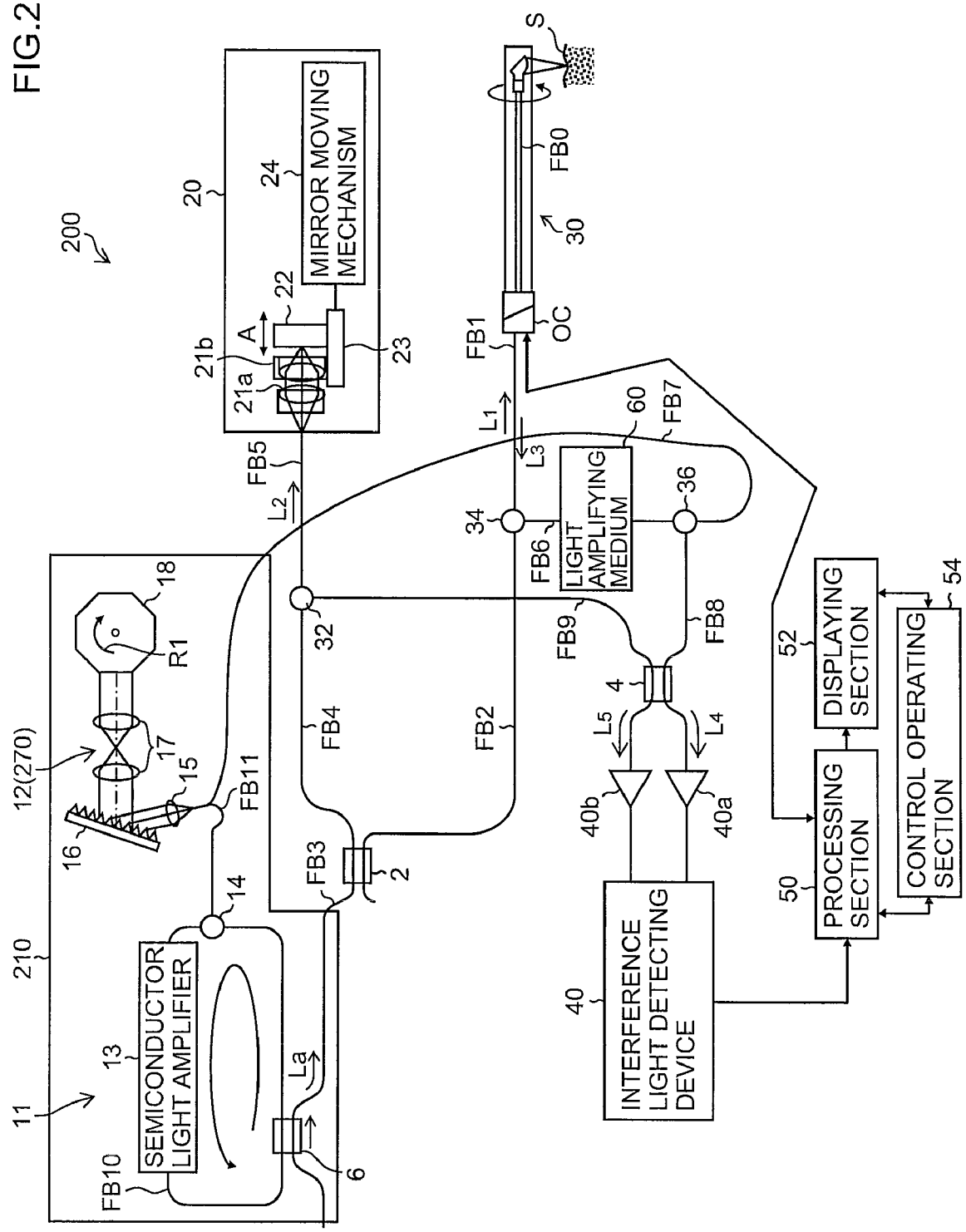
FIG. 2 is a schematic configuration diagram of an optical tomographic imaging apparatus according to a second embodiment of the present invention.

FIG. 2 shows a schematic configuration of an optical tomographic imaging apparatus according to the second embodiment of the present invention.

The second embodiment is similar to the first embodiment described above in that a rotary polygon mirror is shared between a wavelength sweeping light source filter (wavelength selecting device 12) and the light amplifying section filtering mechanism 70. However, instead of separately providing the filtering mechanism 70 having a configuration similar to the wavelength selecting device 12 including the collimator lens 15, the diffraction grating element 16 and the optical system 17 as is the case in the first embodiment, the second embodiment is configured so that the configuration of the light amplifying section filtering mechanism 270 is combined with the wavelength selecting device 12, and the wavelength sweeping light source filter (wavelength selecting device 12) and the light amplifying section filtering mechanism 270 differentiatingly (separately) use an upper part and a lower part of one face of the rotary polygon mirror 18.

As shown in FIG. 2, an optical tomographic imaging apparatus 200 according to the present embodiment differs from the first embodiment shown in FIG. 1 only in that a light amplifying section filtering mechanism 270 is shared with the wavelength sweeping light source filter (wavelength selecting device 12) of a light source unit 210. Otherwise, the configuration is the same as that of the first embodiment.

Therefore, a detailed description will be given on the light amplifying section filtering mechanism 270 shared with the wavelength selecting device 12 of the light source unit 210 while descriptions on other components will be omitted.

Figure 3:
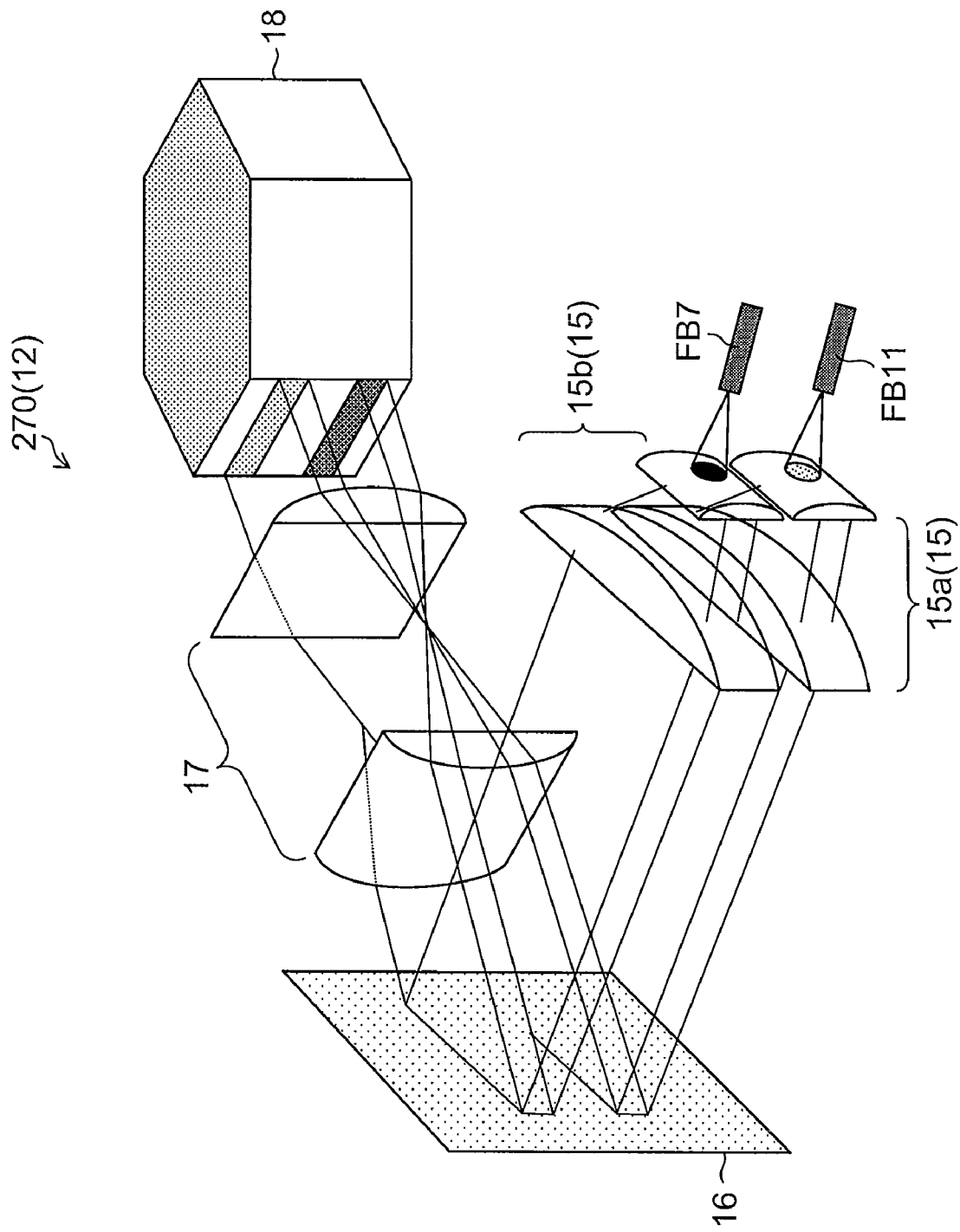
FIG. 3 is a configuration diagram showing a filtering mechanism of the optical tomographic imaging apparatus according to the second embodiment.

FIG. 3 shows a configuration of the filtering mechanism 270.

As shown in FIG. 3, the filtering mechanism 270 according to the second embodiment is shared by the wavelength selecting device 12 of the light source unit 210 and includes: a collimator lens 15; a diffraction grating element 16; an optical system (optical face tangle error correcting lens) 17; and a rotary polygon mirror (polygon mirror) 18.

However, in the present embodiment, the collimator lens 15 is configured to have two separate upper and lower stages of: a collimator lens 15a to which a light beam enters from the wavelength sweeping laser light source resonator of the light source unit 210 via an optical fiber FB11; and a collimator lens 15b to which a light beam enters from an optical fiber FB7 that guides a reflected light beam L3 amplified by a light amplifying medium 60.

Light beams emitted from the optical fiber FB11 and the optical fiber FB7 respectively enter upper and lower portions of the same face of the rotary polygon mirror 18 via the collimator lenses 15a and 15b, the diffraction grating element 16, and the optical system 17, and after being reflected, return along the same paths to respectively reenter the optical fiber FB11 and the optical fiber FB7.

Accordingly, as far as the wavelength selecting device 12 is concerned, only a light beam of a specific frequency range among light beams separated by the diffraction grating element 16 is reflected off of the upper part (portion) of a face of the rotary polygon mirror 18 and once again returns to the optical fiber FB11 to emit a laser beam La of a specific frequency range from the light source unit 210.

Meanwhile, as far as the filtering mechanism 270 is concerned, a reflected light beam L3 amplified by the light amplifying medium 60 is reflected off of the lower part of the same face of the rotary polygon mirror 18, after filtering out an unnecessary spontaneous emission light beam. Subsequently, the reflected light beam L3 once again returns to the optical fiber FB7 to be multiplexed with the reference light beam L2.

Accordingly, similarly with the present embodiment, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized.

A third embodiment of the present invention will now be described.

Figure 4:
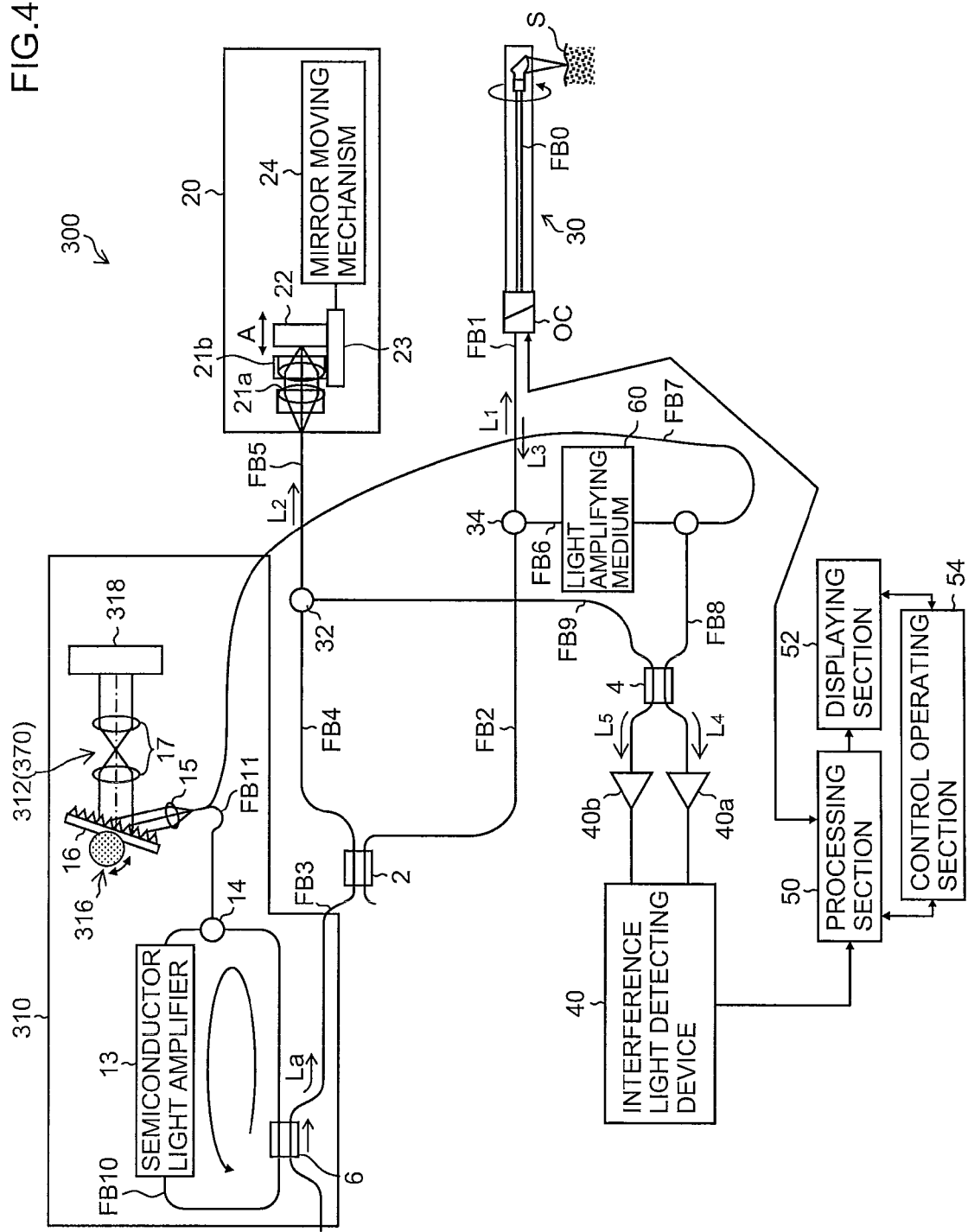
FIG. 4 is a schematic configuration diagram of an optical tomographic imaging apparatus according to a third embodiment of the present invention.

FIG. 4 shows a schematic configuration of an optical tomographic imaging apparatus according to the third embodiment of the present invention.

The third embodiment is arranged so that a light amplifying section filtering mechanism is combined with a wavelength sweeping light source filter (wavelength selecting device) in the same manner as the second embodiment described above. However, the third embodiment is arranged so that a fixed reflecting mirror is used instead of a rotary polygon mirror and a diffraction grating element is rotationally moved by a galvano scanner.

As shown in FIG. 4, an optical tomographic imaging apparatus 300 according to the present embodiment is arranged so that a wavelength selecting device 312 that is a wavelength sweeping light source filter combined with a light amplifying section filtering mechanism 370 that amplifies reflected light beams, in a light source unit 310. Otherwise, the configuration is the same as that of the second embodiment described above. Therefore, a detailed description will be given on the configuration of the wavelength selecting device 312 combined with the filtering mechanism 370, while descriptions on other components will be omitted.

Figure 5:
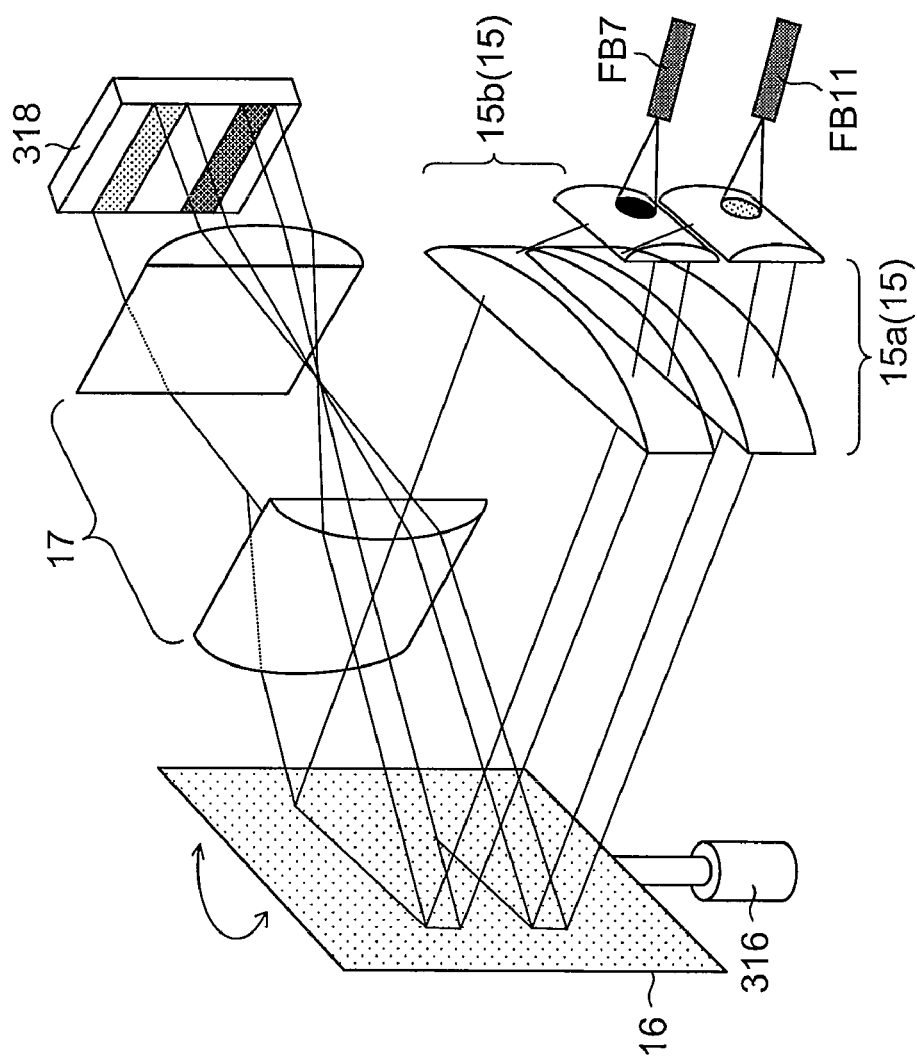
FIG. 5 is a configuration diagram showing a wavelength selecting device combined with a filtering mechanism according to the third embodiment.

FIG. 5 shows a configuration of the wavelength selecting device 312 combined with the filtering mechanism 370.

As shown in FIG. 5, the configuration of the wavelength selecting device 312 combined with the filtering mechanism 370 includes: a collimator lens 15; a diffraction grating element 16; an optical system (optical face tangle error correcting lens) 17; and a fixed reflecting mirror 318.

The collimator lens 15 is dived into two upper and lower parts (portions) in the same manner as the second embodiment described above, and includes: a lower-portion collimator lens 15a to which a light beam enters from an optical fiber FB11 of the light source unit 310; and an upper-portion collimator lens 15b to which a light beam enters from an optical fiber FB7 that guides an amplified reflected light beam L3.

In addition, the diffraction grating element 16 is configured so as to be rotationally movable using a galvano scanner 316. By rotationally moving (rotating) the diffraction grating element 16 using the galvano scanner 316, the same wavelength sweeping effect as the rotary polygon mirror 18 in the previous embodiment is realized in combination with the fixed reflecting mirror 318.

In other words, light beams emitted from the optical fiber FB11 and the optical fiber FB7 respectively enter upper and lower portions of a reflecting face of the fixed reflecting mirror 318 via the collimator lenses 15a and 15b, the diffraction grating element 16 rotationally moved (moved so as to swivel) by the galvano scanner 316, and the optical system 17, and after being reflected, return along the same paths to respectively enter the optical fiber FB11 and the optical fiber FB7.

Accordingly, as far as the wavelength selecting device 312 is concerned, due to the actions of the diffraction grating element 16 rotationally moved by the galvano scanner 316 and of the fixed reflecting mirror 318, only a light beam of a specific frequency range among light beams separated by the diffraction grating element 16 returns to the optical fiber FB11, whereby a laser beam La of a specific frequency range is emitted from the light source unit 310.

Meanwhile, as far as the filtering mechanism 370 is concerned, in the same manner as described above, due to the actions of the diffraction grating element 16 rotationally moved by the galvano scanner 316 and of the fixed reflecting mirror 318, a reflected light beam L3 amplified by the light amplifying medium 60 from which an unnecessary spontaneous emission light beam has been filtered out once again returns to the optical fiber FB7 to be multiplexed with a reference light beam L2.

Accordingly, similarly with the present embodiment, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized.

A fourth embodiment of the present invention will now be described.

Figure 6:
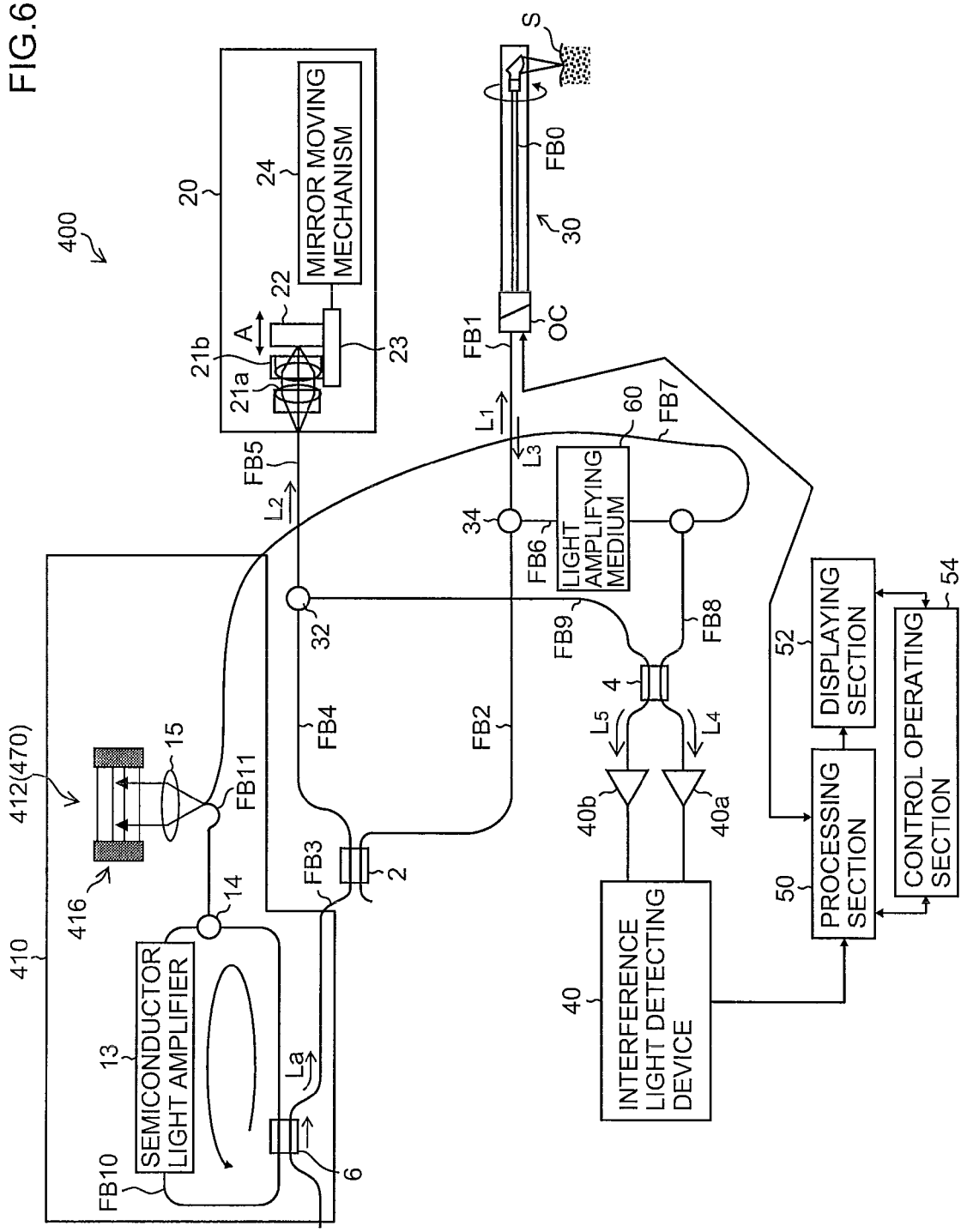
FIG. 6 is a schematic configuration diagram of an optical tomographic imaging apparatus according to a fourth embodiment of the present invention.

FIG. 6 shows a schematic configuration of an optical tomographic imaging apparatus according to the fourth embodiment of the present invention.

The present fourth embodiment is arranged so that a light amplifying section filtering mechanism is shared with a wavelength sweeping light source filter (wavelength selecting device) in the same manner as the second or third embodiment described above. In particular, the present fourth embodiment is arranged so that a Fabry-Perot filter is used as the shared wavelength selecting device of the light source unit and the light amplifying section filtering mechanism.

As shown in FIG. 6, an optical tomographic imaging apparatus 400 according to the present embodiment is arranged such that in a light source unit 410, a wavelength selecting device 412 that is a wavelength sweeping light source filter and a light amplifying section filtering mechanism 470 that amplifies a reflected light beam are configured by a Fabry-Perot filter 416 to be shared. Meanwhile, other components are the same as those of the third embodiment described above. Accordingly, a detailed description will be given on the Fabry-Perot filter 416 that makes up the wavelength selecting device 412 that is the filtering mechanism 470. However, since other components are the same as those of the third embodiment, descriptions thereof will be omitted.

Figure 7:
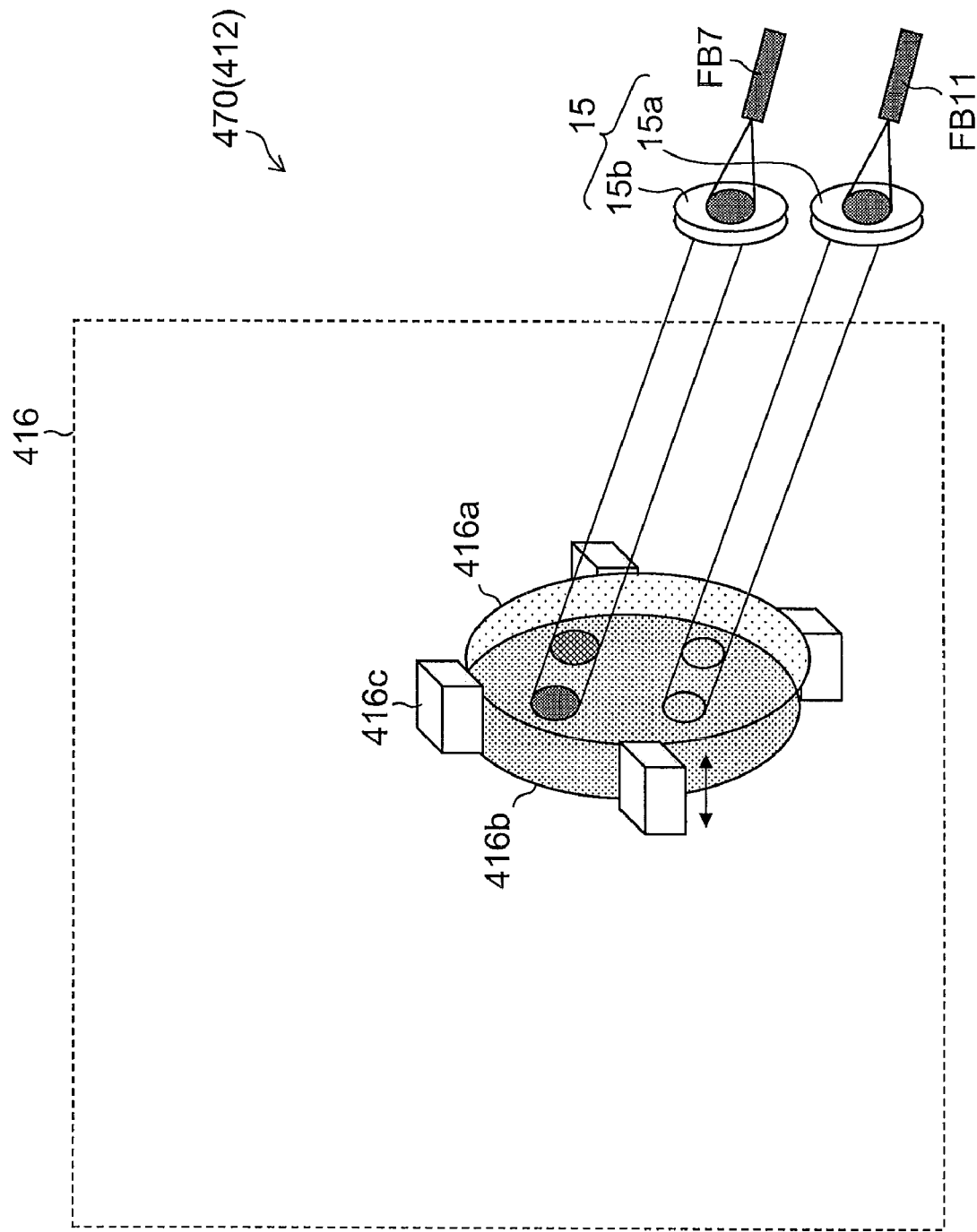
FIG. 7 is a configuration diagram showing a wavelength selecting device combined with a filtering mechanism according to the fourth embodiment.

FIG. 7 shows a configuration of the wavelength selecting device 412 combined with the filtering mechanism 470.

As shown in FIG. 7, the Fabry-Perot filter (Fabry-Perot wavelength-variable filter) 416 is an optical filter in which a gap is formed between a partially reflecting mirror 416a and a total reflecting mirror 416b having a high reflectance, and the mirrors 416a and 416b are arranged so as to oppose each other. A piezoelectric actuator 416c is disposed between the partially reflecting mirror 416a and the total reflecting mirror 416b, and the partially reflecting mirror 416a is displaced in the direction of the total reflecting mirror 416b as indicated by the arrow in the drawing to vary the size of the gap so that a wavelength corresponding to the size of the gap is selected and transmitted.

In addition, while a light beam is arranged so as to enter the Fabry-Perot filter 416 via the collimator lens 15, the collimator lens 15 is configured so that a collimator lens 15a which causes a light beam La to enter from an optical fiber FB11 of the light source unit 410 and a collimator lens 15b that causes a reflected light beam L3 to enter from an optical fiber FB7 are separately configured.

The light beam La entering the Fabry-Perot filter 416 from the optical fiber FB11 via the collimator lens 15a and the reflected light beam L3 entering the Fabry-Perot filter 416 from the optical fiber FB7 via the collimator lens 15b are respectively reflected by the Fabry-Perot filter 416, and only light beams of a specific wavelength return to the optical fiber FB11 and the optical fiber FB7.

Accordingly, the Fabry-Perot filter 416 combines the functions of the wavelength selecting device 412 of the light source unit 410 and of the light amplifying section filtering mechanism 470.

Accordingly, similarly with the present embodiment, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized.

A fifth embodiment of the present invention will now be described.

Figure 8:
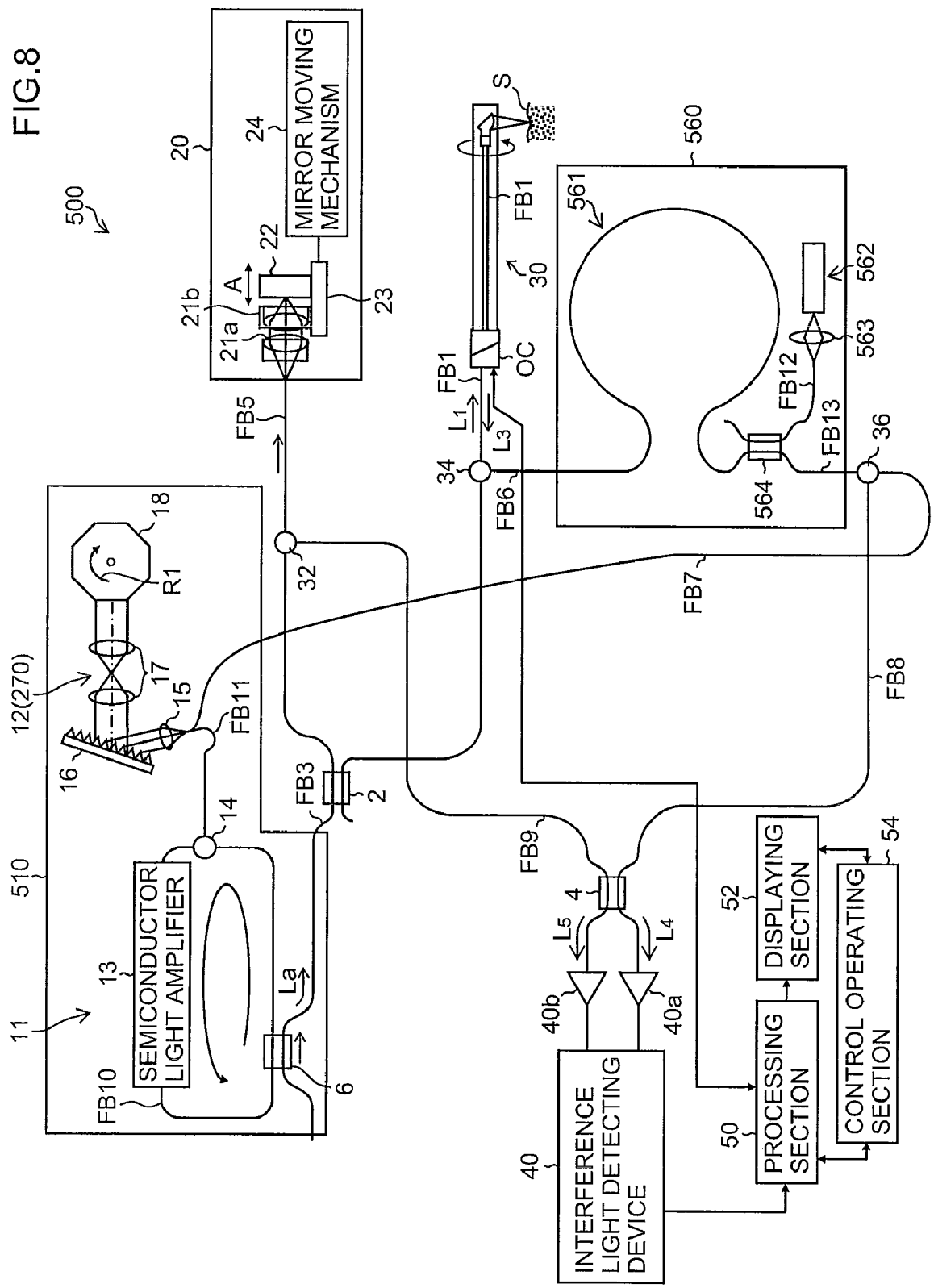
FIG. 8 is a schematic configuration diagram of an optical tomographic imaging apparatus according to a fifth embodiment of the present invention.

FIG. 8 shows a schematic configuration of an optical tomographic imaging apparatus according to the fifth embodiment of the present invention.

The fifth embodiment is arranged so that the light amplifying medium 60 according to the second embodiment shown in FIG. 2, in which the rotary polygon mirror of the wavelength selecting device is shared by the filtering mechanism, specifically is configured with an optical fiber amplifier.

That is, as shown in FIG. 8, the present fifth embodiment is exactly the same as the second embodiment shown in FIG. 2 except that a light amplifying medium 560 that takes the form of an optical fiber amplifier. A filtering mechanism 570 that filters out an unnecessary spontaneous emission light beam from a reflected light beam L3 amplified by the light amplifying medium 560 is configured so as to be shared with a wavelength selecting device (wavelength sweeping light source filter) 12 of a light source unit 510. Therefore, a detailed description of components other than the light amplifying medium 560 will be omitted.

As shown in FIG. 8, the light amplifying medium 560 is provided at an optical fiber FB6 connected to an optical branching unit 34 and which guides the reflected light beam L3 from a measurement subject S. The reflected light beam L3 amplified by the light amplifying medium 560 is to be guided from an optical light beam FB7 to the filtering mechanism 570 via an optical branching unit 36.

The light amplifying medium 560 includes: a fiber amplifying section 561 which, upon the entrance of a signal light beam in an excited state, amplifies the signal light beam; a YAG laser (excitation laser) 562 which generates a wavelength of 1.06 μm that is an excitation light beam to be supplied to the fiber amplifying section 561; a collecting lens 563 which collects the excitation light beam outputted from the YAG laser 562; an optical fiber FB12 which guides the excitation light beam; and an optical fiber coupler 564 which guides the excitation light beam guided by the optical fiber FB12 to the fiber amplifying section 561. The fiber amplifying section 561 includes an optical fiber whose core is impregnated with $Ti^{4+}$ having a gain in the vicinity of 780 nm, whereby the optical fiber is provided in a rolled-up state.

Next, operations of the light amplifying medium 560 made up of an optical fiber amplifier will be described.

An excitation light beam with a wavelength of 1.06 μm emitted from the YAG laser 562 is collected by the collecting lens 563 and enters the optical fiber FB12. The excitation light beam enters the fiber amplifying section 561 via the optical fiber coupler 564. The excitation light beam is absorbed by the $Ti^{4+}$ impregnating the core while propagating inside the fiber amplifying section 561. Having absorbed the excitation light beam, the $Ti^{4+}$ transitions from a ground state to an excited state. In this state, a reflected light beam L3 enters one end of the fiber amplifying section 561. As the reflected light beam L3 propagates through the fiber amplifying section 561, induced emission of a light beam with the same phase as the reflected light beam L3 occurs, thereby restoring the $Ti^{4+}$ to the ground state. Through repetition of such induced emission, the amplified reflected light beam L3 is emitted from the other end of the fiber amplifying section 561.

Therefore, as described above, the amplified reflected light beam L3 emitted from the light amplifying medium 560 is guided to the filtering mechanism 570 via the optical fiber FB7 to filter out an unnecessary spontaneous emission light beam, and then guided to an optical multiplexing device 4 via the optical fiber FB8 to be multiplexed with a reference light beam L2. Since the light beam to be multiplexed with the reference light beam L2 is a signal that is an amplification of the reflected light beam L3 and therefore has the same phase as the reflected light beam L3, tomographic image information can be acquired from an interference light beam created by causing interference of the amplified reflected light beam L3 and the reference light beam L2.

Accordingly, similarly with the present embodiment, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized.

A sixth embodiment of the present invention will now be described.

Figure 9:
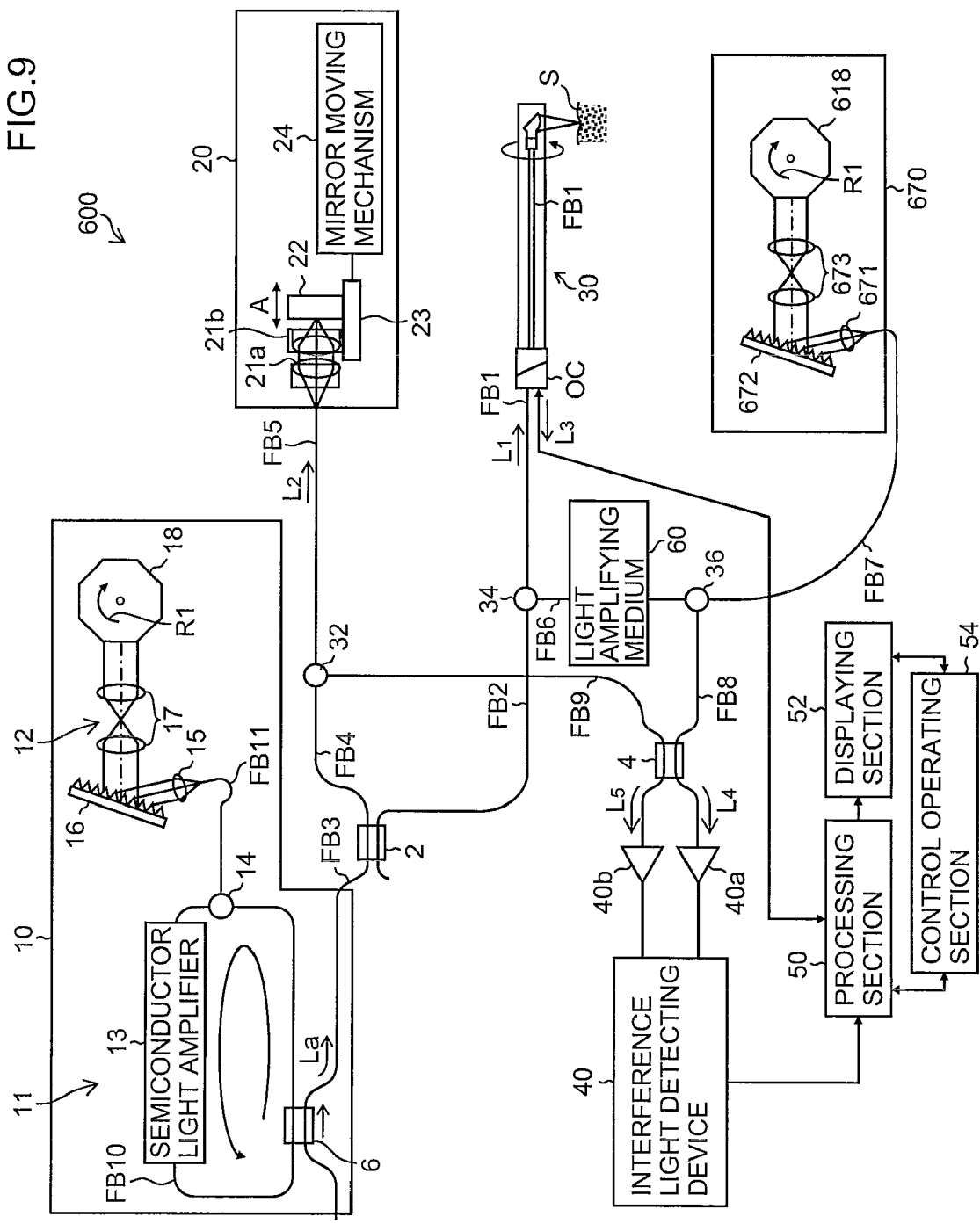
FIG. 9 is a schematic configuration diagram of an optical tomographic imaging apparatus according to a sixth embodiment of the present invention.

FIG. 9 shows a schematic configuration of an optical tomographic imaging apparatus according to the sixth embodiment of the present invention.

The sixth embodiment is comparable to the first embodiment described earlier. That is, while only the rotary polygon mirror 18 is shared (albeit different faces are respectively used) between the wavelength selecting device 12 of the light source unit 10 and the light amplifying section filtering mechanism 70 in the first embodiment, the sixth embodiment is arranged so that a wavelength selecting device and a filtering mechanism have separate rotary polygon mirrors.

As shown in FIG. 9, an optical tomographic imaging apparatus 600 according to the sixth embodiment is approximately the same as the configuration according to the first embodiment shown in FIG. 1; except that a filtering mechanism 670 according to the sixth embodiment corresponding to the filtering mechanism 70 according to the first embodiment includes a rotary polygon mirror 618 separate from the rotary polygon mirror 18 of the wavelength selecting device 12 of the light source unit 10.

That is, the filtering mechanism 670 according to the present embodiment is configured so as to include: a collimator lens 671; a diffraction grating element 672; an optical system (optical face tangle error correcting lens) 673; and a rotary polygon mirror (polygon mirror) 618.

Moreover, in the case of the present embodiment, since a light source section filter (wavelength selecting device 12) and a light amplifying section filter (filtering mechanism 70) are completely separate, it becomes more important that the positional relationships between the reflecting faces of the respective rotary polygon mirrors 18 and 618, and the diffraction grating elements 16 and 672 and optical fibers FB11 and FB7 are synchronized to be temporally consistent than in cases where filters are shared, as in the respective embodiments described earlier. Accordingly, synchronization control, not shown, is performed.

Figure 10A:
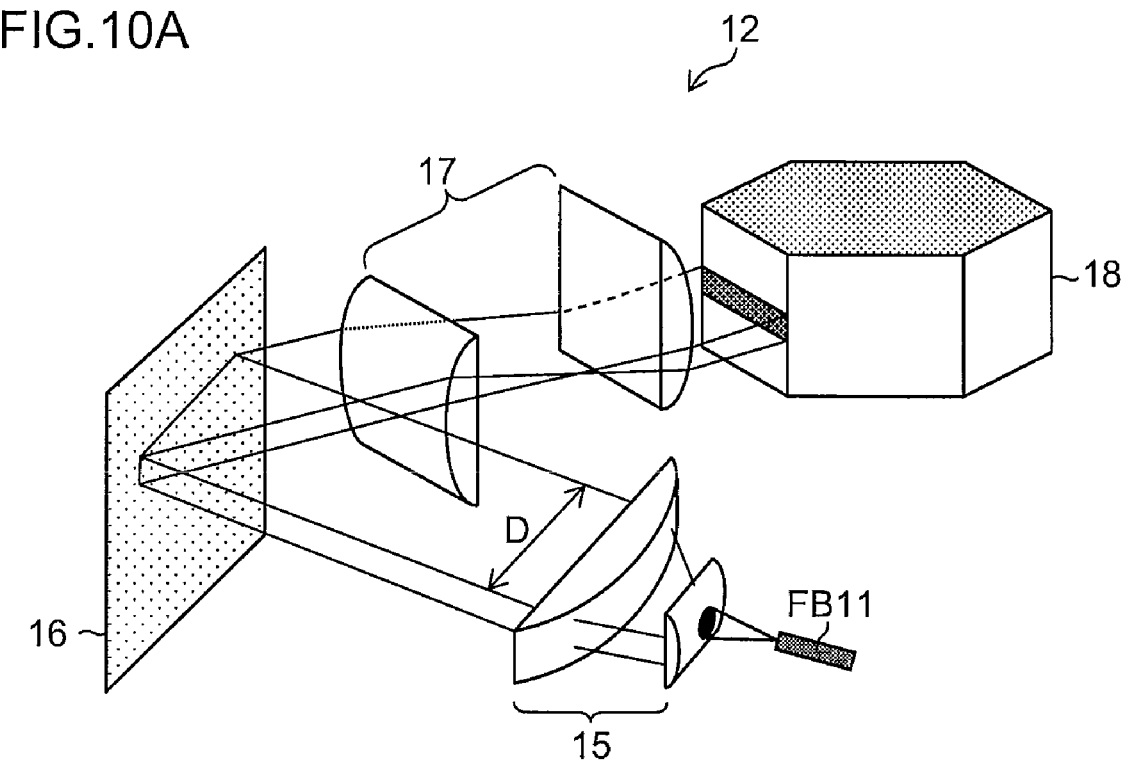
Figure 10B:
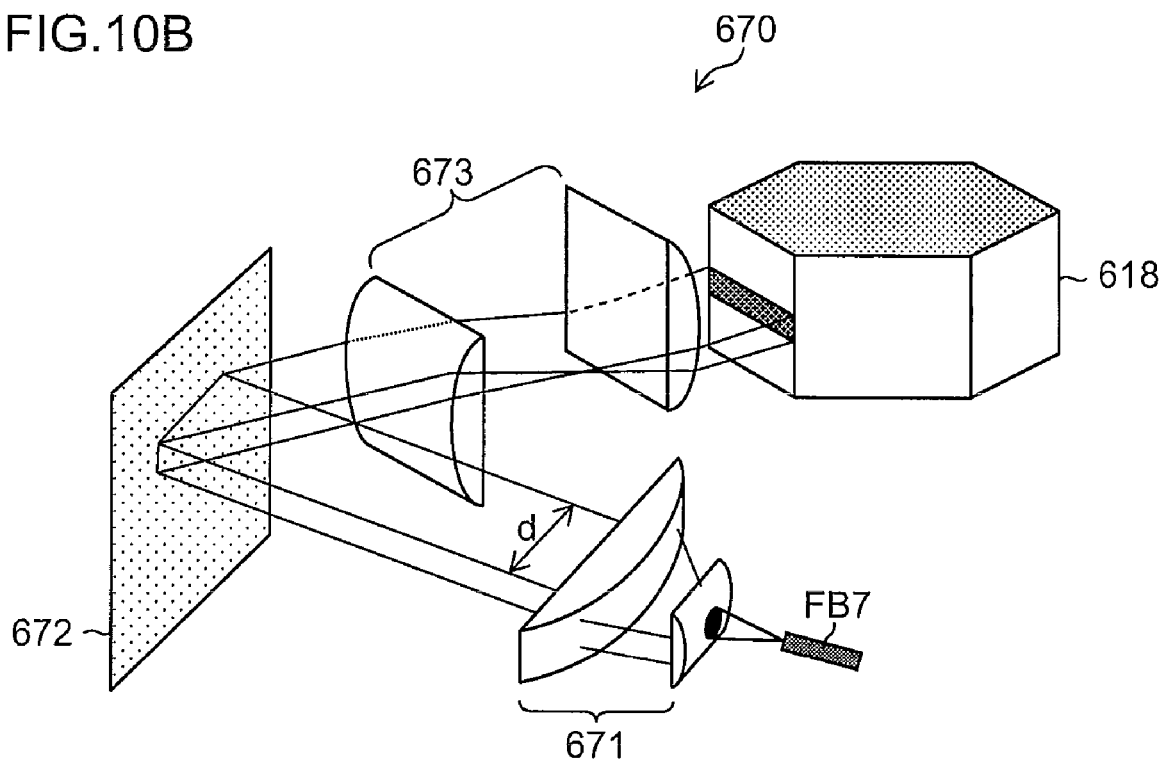
FIG. 10B is a configuration diagram showing a filtering mechanism according to the sixth embodiment.

Detailed configurations of the filters are shown in FIG. 10. FIG. 10A shows a configuration of the wavelength selecting device 12 of the light source unit 10, while FIG. 10B shows a configuration of the light amplifying section filtering mechanism 670.

As shown in FIG. 10A, the wavelength selecting device 12 is arranged so that a light beam enters from the optical fiber FB11 that guides a light beam from inside a wavelength sweeping laser light source resonator to the collimator lens 15. The light beam is converted into a parallel light beam by the collimator lens 15, and subsequently enters the diffraction grating element 16. A beam width entering the diffraction grating element 16 is hereby designated by D.

The light beam having entered the diffraction grating element 16 enters the rotary polygon mirror 18 via the optical system 17 to be reflected and returned along the same path, and reenters the optical fiber FB11.

In addition, as shown in FIG. 10B, the filtering mechanism 670 is arranged so that a light beam enters from the optical fiber FB7 that guides a light beam (amplified reflected light beam L3) from the light amplifying medium 60 to the collimator lens 671. The light beam is converted into a parallel light beam by the collimator lens 671, and subsequently enters the diffraction grating element 672. A beam width entering the diffraction grating element 672 is hereby designated by d.

The light beam having entered the diffraction grating element 672 enters the rotary polygon mirror 618 via the optical system 673 to be reflected and returned along the same path, and reenters the optical fiber FB7.

In this case, the beam width D to enter the diffraction grating element 16 of the wavelength selecting device 12 is to be greater than the beam width d to enter the diffraction grating element 672 of the filtering mechanism 670 or, in other words, so that D>d is true. Accordingly, the transmission band of the light amplifying section filter (filtering mechanism 70) is to be wider than the transmission band of the light source section filter (wavelength selecting device 12).

Figure 11:
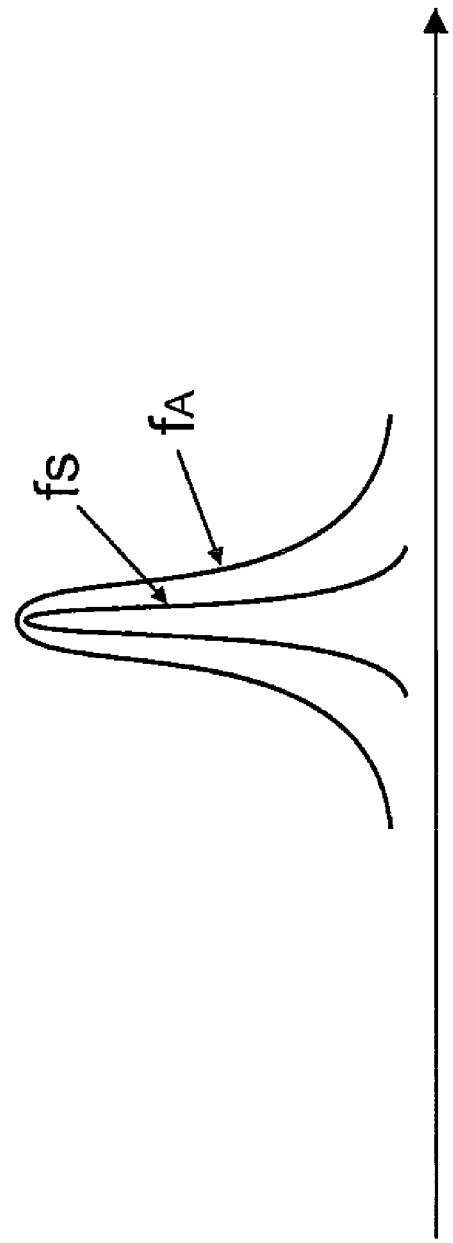
FIG. 11 is a graph showing filter transmission band characteristics of the wavelength selecting device and the filtering mechanism according to the sixth embodiment.

FIG. 11 shows transmission band characteristics of the light source section filter (wavelength selecting device 12) and the light amplifying section filter (filtering mechanism 70) in this case. In FIG. 11, reference character $f_S$ designates transmission band characteristics of the light source section filter while reference character $f_A$ designates transmission band characteristics of the light amplifying section filter.

As shown in FIG. 11, the transmission band of the light amplifying section filter (filtering mechanism 70) is to be wider than the transmission band of the light source section filter (wavelength selecting device 12). In this manner, even when separately configuring the light source section filter (wavelength selecting device 12) and the light amplifying section filter (filtering mechanism 70) as is the case with the present embodiment, synchronization can be reliably achieved by slightly increasing the width of an amplifying-side filter so as to bring the accuracy of synchronization within a practical range.

Similarly with the present embodiment, since a spontaneous emission light beam from a light amplifying medium unnecessary for interference can be blocked, S/N deterioration due to fluctuations in the spontaneous emission light beam can be prevented and S/N enhancement equivalent to a gain of a light amplifying section can be realized.

The present invention has been devised so as to enhance S/N by amplifying a reflected light beam from a measurement subject and filtering off an unnecessary spontaneous emission light beam generated at a light amplifying section using a filtering mechanism. While examples have been shown in the embodiments described above in which a semiconductor gain medium or an optical fiber amplifier is used as the light amplifying section and a polygon mirror, a galvano scanner, a Fabry-Perot filter or the like is used as a filter of the amplifying section filtering mechanism, combinations thereof are not limited to those shown in the embodiments described above, and any combination other than the respective embodiments can be used.

Although the optical tomographic imaging apparatus according to the present invention has been described in detail, it is understood that the present invention is not limited to the examples shown above and that various changes and modifications can be made without departing from the scope thereof.

What is claimed is:

1. An optical tomographic imaging apparatus comprising:
    a light source unit including a light source that emits a light beam having a certain wavelength band, and a wavelength selecting device as a light source section filter that selects a wavelength of the light beam emitted from the light source;
    a light splitting device that splits the light beam emitted from the light source unit into a measurement light beam and a reference light beam;
    an optical path length adjusting device that adjusts an optical path length of the reference light beam split by the light splitting device;
    a light amplifying device that amplifies a reflected light beam from a measurement subject when the measurement light beam split by the light splitting device is irradiated on the measurement subject;
    an amplifying section filtering mechanism having a filter characteristic identical to a time variation characteristic of the light source section filter, and which selects a specific wavelength from the amplified reflected light beam;
    an optical multiplexing device that multiplexes the reflected light beam from which the specific wavelength has been selected by the amplifying section filtering mechanism with the reference light beam whose optical path length has been adjusted by the optical path length adjusting device;
    an interference light detecting device that detects an interference light beam between the reflected light beam and the reference light beam multiplexed by the optical multiplexing device; and
    an image acquiring device that acquires a tomographic image of the measurement subject from the interference light beam detected by the interference light detecting device.

2. The optical tomographic imaging apparatus according to claim 1, wherein the wavelength selecting device as the light source section filter and the amplifying section filtering mechanism are separately configured.

3. The optical tomographic imaging apparatus according to claim 1, wherein the wavelength selecting device as the light source section filter and the amplifying section filtering mechanism share at least a part of each other.

4. The optical tomographic imaging apparatus according to claim 1, wherein the wavelength selecting device as the light source section filter and the amplifying section filtering mechanism use polygon mirrors.

5. The optical tomographic imaging apparatus according to claim 3, wherein the wavelength selecting device as the light source section filter and the amplifying section filtering mechanism share a polygon mirror and respectively use different faces of the polygon mirror.

6. The optical tomographic imaging apparatus according to claim 3, wherein the wavelength selecting device as the light source section filter and the amplifying section filtering mechanism share a polygon mirror and use one face of the polygon mirror, differentiatingly using an upper part and a lower part of the one face.

7. The optical tomographic imaging apparatus according to claim 1, wherein the wavelength selecting device as the light source section filter and the amplifying section filtering mechanism use galvano scanners.

8. The optical tomographic imaging apparatus according to claim 1, wherein the wavelength selecting device as the light source section filter and the amplifying section filtering mechanism use Fabry-Perot filters.

9. The optical tomographic imaging apparatus according to claim 1, wherein a transmission band of the amplifying section filtering mechanism is wider than a transmission band of the wavelength selecting device as the light source section filter.

10. The optical tomographic imaging apparatus according to claim 1, wherein the light amplifying device is a semiconductor gain medium.

11. The optical tomographic imaging apparatus according to claim 1, wherein the light amplifying device is an optical fiber amplifier.

12. An optical tomographic imaging method comprising:

emitting a light beam having a certain wavelength band from a light source;

selecting a wavelength of the light beam emitted from the light source by a light source section filter;

splitting the light beam emitted from the light source into a measurement light beam and a reference light beam;

adjusting an optical path length of the reference light beam;

amplifying a reflected light beam from a measurement subject when the measurement light beam is irradiated on the measurement subject;

selecting a specific wavelength from the amplified reflected light beam by an amplifying section filtering mechanism having a filter characteristic identical to a time variation characteristic of the light source section filter;

multiplexing the reflected light beam from which the specific wavelength has been selected with the reference light beam whose optical path length has been adjusted;

detecting an interference light beam between the reflected light beam and the reference light beam which have been multiplexed; and acquiring a tomographic image of the measurement subject from detected the interference light beam.

* * * * *